United States Patent [19]
Karimian

[11] Patent Number: 5,610,292
[45] Date of Patent: Mar. 11, 1997

[54] PROCESS FOR PRODUCING 2,2'-O-CYCLONUCLEOSIDES NUCLEOSIDES, AND ANALOGS THEREOF

[75] Inventor: Khashayar Karimian, Brantford, Canada

[73] Assignee: ACIC (Canada) Inc., Brantford, Canada

[21] Appl. No.: 313,579

[22] Filed: Sep. 27, 1994

Related U.S. Application Data

[62] Division of Ser. No. 930,606, filed as PCT/CA91/00077, Mar. 13, 1991, abandoned.

[30] Foreign Application Priority Data

Mar. 13, 1990 [CA] Canada .................................. 2012093
Mar. 13, 1990 [CA] Canada .................................. 2012094

[51] Int. Cl.$^6$ ........................ C07H 19/06; C07H 19/067
[52] U.S. Cl. .................... 536/55.3; 536/28.5; 536/28.52
[58] Field of Search ............................. 536/28.5, 28.52, 536/55.3

[56] References Cited

U.S. PATENT DOCUMENTS

| 4,652,554 | 3/1987 | Chwang | 536/28.53 |
| 5,399,682 | 3/1995 | Karimian et al. | 536/55.3 |

OTHER PUBLICATIONS

Hamamura et al. J. Med. Chem. 19(5) (1976), pp. 667–674.
Divakar et al. J. Chem. Soc Perkins Trans I, (1982) (5), pp. 1171–1176.
Gosselin et al. J. Med. Chem. 29 (1986), pp. 203–213.
D. Wagner et al. "Preparation & synthetic utility . . . " The Jour. of Organic Chemistry, vol. 39 No. 1, Jan. 1974, pp. 24–30.
Chemical Abstracts, vol. 86 No. 16, 18 Apr. 1977 #121712t. Columbus, Ohio, p. 583.
H. P. M. Fromageot et al. "$N^4O^{3'}$, $O^{5'}$ –triacetyl . . . " Tetrahedron Letters, No. 29, 1966, Pergamon Press Ltd. (GB), pp. 20–25.

*Primary Examiner*—James O. Wilson
*Attorney, Agent, or Firm*—Nixon & Vanderhye

[57] ABSTRACT

A novel process is provided for producing a nucleoside, such as cytarabine, or a nucleoside analogue, comprising the step of reacting 2,2'-O-cyclonucleoside or an analogue thereof with an amine. Preferably, the process is conducted in the presence of an aqueous solvent. A novel process for the production of the precursor 2,2'-O-cyclonucleoside compounds and pharmaceutically acceptable salts thereof is also provided which comprises reacting a 2,3'-O-diaikylstannylene nucleoside compound with an amine in the presence of a sulfonyl compound. Cytarabine is a known antineoplastic and antiviral agent.

29 Claims, No Drawings

PROCESS FOR PRODUCING 2,2'-O-CYCLONUCLEOSIDES NUCLEOSIDES, AND ANALOGS THEREOF

This is a Rule 60 Divisional of application Ser. No. 07/930,606, filed as PCT/CA91/00077, Mar. 13, 1991, now abandoned.

TECHNICAL FIELD

The present invention relates to a novel process for the production of nucleosides, nucleoside analogues and pharmaceutically acceptable salts thereof which includes, in one aspect of the invention, a novel process for producing cyclonucleosides, specifically 2,2'-o-cyclonuclcosides, cyclonucleoside analogues and pharmaceutically acceptable salts thereof.

BACKGROUND ART

Cytarabine, a specific nucleoside compound, is a known antineoplastic and antiviral agent. Cytarabine, which is also known as 4-amino-1-β-D-arabino-pentofuranosyl-2(1H)-pyrimidinone, 1-β-D-arabino-pentofuranosylcytosine and β-cytosinearabinoside, has the following chemical structure:

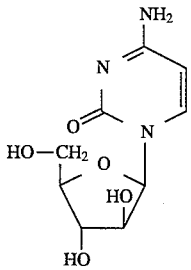

Ogilvie (*Carbohyd. Res.*, 24, 210 (1972)) teaches the production of cytanbine from cytidine. Specifically, the process comprises reacting cytidine with diphenyl carbonate and sodium hydrogen carbonate at 150° C in DMF. The product cytarabine was purified using thin layer chromatography and obtained in a yield of 40%.

Beranek et al (*Nucleic Acid Chemistry*, Vol. 1, 249, Edited by Townsend and Tipson, Wiley, N.Y.) teach the production of cytarabine from cytidine. Specifically, cytidine is reacted with incremental amounts of diphenyl carbonate in the presence of DMF and water at 120° C. The overall yield of pure cytarabine was limited to 31.9%.

Roberts et al (*J. Org. Chem.* 32, 816 (1967)) teach the production of cytarabine from cytidine (or from 2'(3')-cytidylic acid). Specifically, cytidine is reacted with phosphoric acid at 80° C. for a period of 30 hours to produce a 2,2'-O-cyclocytidine analogue intermediate. This intermediate is then hydrolyzed at a pH of 9 utilizing lithium hydroxide to produce the 3',5'-diphosphate of cytarabine. The diphosphate is then treated with magnesium chloride, ammonium chloride and concentrated ammonium hydroxide, and thereafter purified by column chromatography to yield pure cytarabine. The overall yield of pure cytarabine is limited to 53% based on the unrecovered portion of the starting cytidine.

Kikugawa et al (*J. Org. Chem.*, 37, 284–288 (1972)) teach the conversion of 2,2'-O-cyclocytidine hydrochloride to cytarabine. Specifically, ammonia is added to an aqueous solution of 2,2'-O-cyclocytidine thereby raising the pH to 9. The solution is thereafter acidified with hydrochloric acid and run through an ion exchange column. Thereafter, cytarabine is crystallized from ethanol in a yield of 90%.

Sowa et al (*Bull. Chem. Soc. Jap.*, 48, 505–507 (1975)) teach the production of cytarabine from 2,2'-O-cyclocytidine. Specifically, sodium hydroxide is added to an aqueous solution of 2,2'-O-cyclocytidine hydrochloride thereby raising the pH of the solution to 10. Thereafter, the solution is run through a $H^+$ ionic exchange resin followed by recrystallization of pure cytarabinc from ethanol.

Further, the production of cyclonucleosides is known. For example, Walwick et al (*Proc. Chem. Soc.*, 84 (1959)) teach the production of 2,2'-O-cyclocytidine hydrochloride from cytidine. The process involved heating cytidine with polyphosphoric acid followed by dephosphorylation of one of the reaction products, 2,2'-O-cyclocytidine-3',5'-diphosphate.

Doerr et al (*J. Org. Chem.*, 32, 1462 (1967)) teach the production of 2,2'-O-cyclocytidine chloride from uridine using a process comprising six steps. It is interesting to note that in the final step, 2,2'-O-cyclotidine hydrochloride was obtained only in a 57% yield. Taking into account the fact that each step is not quantitative, the overall yield of 2,2'-O-cyclocytidine hydrochloride from uridine can be expected to be on the order of from 10% to 20%.

Kikugawa et al (*Tet. Lett.*, 869 (1970)) teach the production of the hydrochloride or the formate salt of 2,2'-O-cyclocytidine. Specifically, the process comprises reacting cytidine with thionyl chloride and N,N'-dimethylfonnamide. It is interesting to note that the crude 2,2'-O-cyclocytidine salt was obtained in a yield of only 30.4%. Kikugawa et al (*J. Org. Chem.*, 37, 284 (1972)) also provide an improved process for preparing 2,2'-O-cyclocytidine. The improvement appears to relate to an improved yield (55%) of the product using ion exchange and chromatography techniques.

Sowa et al (*Bull. Chem. Soc. Jap.*, 48, 505 (1975)) teach a process for the production of cyclonuclcosides which comprises reacting the starting ribonucleoside with thionyl chloride and water and subsequently refluxing the reaction mixture at an acidic pH. It is interesting to note that a yield of about 73 % of 2,2'-O-cyclocytidine hydrochloride was allegedly obtained whereas a yield of about 47% of 2,2'-cyclouridine hydrochloride was allegedly obtained.

Yamaguchi et al (*J. Med. Chem.*, 19, 654 (1979)) teach the production of 2,2'-O-cyclocytidine hydrochloride via reaction of cytidine with an organic acid chloride.

The aforementioned prior art techniques for the preparation of 2,2'-cyclonucleosides are deficient in that they require multiple steps with inherent loss of yield and/or they require silica/resin columns for isolation and purification. Furthermore, the prior art processes for the production of cytarabine and its analogues are deficient in that the purified product is obtained in a relatively low yield and/or the process is complicated requiting a series of steps including the use of ion exchange resins.

h would be desirable to have a relatively simple process for producing 2,2'-O-cyclonucleosides in acceptable and/or comparable yields. Furthermore, it would be desirable to have a process for the production of 2,2'-O-cyclonucleosides such as cytarabine and pharmaceutically acceptable salts thereof in relatively high yields and by a relatively simple process.

SUMMARY OF THE INVENTION

It is an object of the present invention to provide a novel process for the production of nucleotides, nucleoside analogues and pharmaceutically acceptable salts thereof.

It is another object of the present invention to provide a novel process for the production of cytarabine, cytarabine analogues and pharmaceutically acceptable salts thereof.

It is another object of the present invention to provide a novel process for the production of 2,2'-O-cyclonucleoside compounds and pharmaceutically acceptable salts thereof.

It is yet another object of the present invention to provide a novel process for the production of 2,2'-O-cyclocytidine compounds and pharmaceutically acceptable salts thereof.

Accordingly, the present invention provides a process for directly preparing a compound of Formula I, or a pharmaceutically acceptable salt thereof:

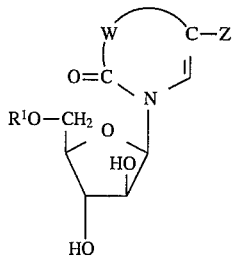

which comprises the step of reacting (i) a compound of Formula II or a pharmaceutically acceptable salt thereof:

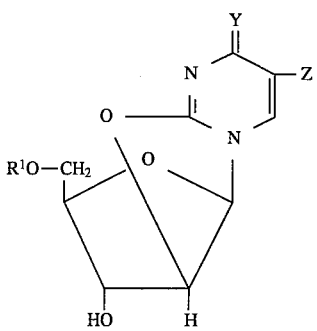

wherein $R^1$ is selected for the group comprising hydrogen, trityl, methoxytrityl, dimethoxytrityl, acetyl, a $C_2$–$C_6$ alkylacyl group, a $C_6$–$C_9$ arylacyl group, allyl, 2,2,2-trichloroethyl, phosphates and salts thereof, tosyl and mesyl; W is selected from the group comprising —NH—CO— and —NH—C(NH$_2$)—; Z is selected from the group comprising hydrogen and methyl; and Y is selected from the group comprising —N(H)— or O; with (ii) an amine selected from the group comprising $C_5$–$C_{12}$ heterocyclic amines and amines having the general formula $R^2R^3R^4N$ wherein $R^2$, $R^3$ and $R^4$ can be the same or different and are selected from the group comprising hydrogen, a $C_1$–$C_6$ alkyl group and a $C_6$–$C_9$ aryl group, with the proviso that the each of $R^2$, $R^3$ and $R^4$ is not hydrogen.

In another aspect of the present invention a process for producing a compound of Formula II:

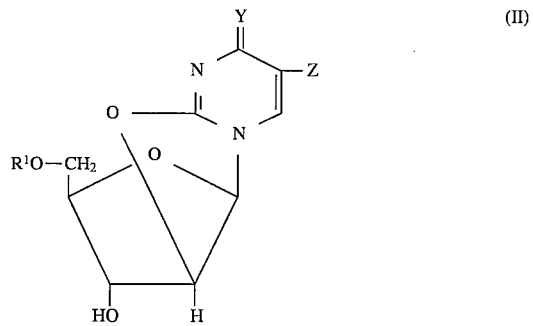

or a pharmaceutically acceptable salt thereof is provided which comprises the step of reacting (i) a compound of Formula III:

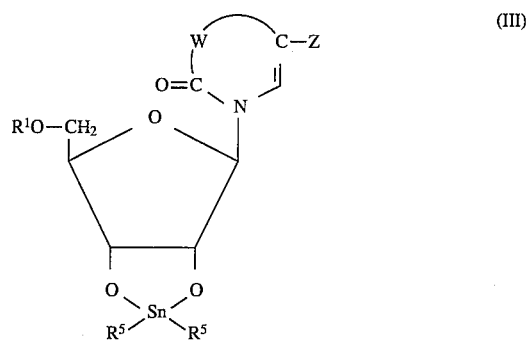

wherein $R^1$, W and Z are as defined above and $R^5$ is a $C_1$–$C_6$ alkyl group, with (ii) an amine selected from pyridine and amines having the general formula $Q^2Q^3Q^4N$ wherein $Q^2$, $Q^3$ and $Q^4$ can be the same or different and are is selected from the group comprising a $C_1$–$C_6$ alkyl group and a $C_6$–$C_9$ aryl group, in the presence of (iii) a sulfonyl compound having the general formula $R^6SO_2X$ wherein $R^6$ is selected from the group comprising —$CF_3$, a $C_1$–$C_6$ alkyl group and $C_6$–$C_9$ aryl group, and X is selected from a halogen and $SO_3CF_3$, to produce a compound of Formula II.

In another aspect of the present invention a process for producing a compound of Formula II:

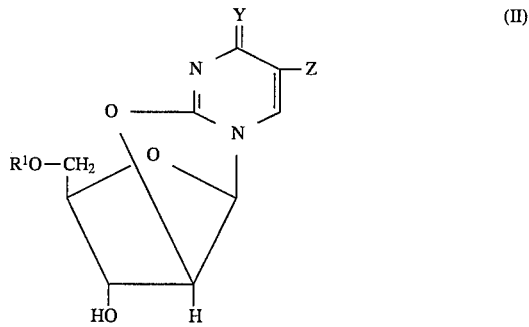

wherein Y is —N(H)— and Z is hydrogen, or a pharmaceutically acceptable salt thereof, is provided which comprises the step of reacting (i) a compound of Formula III:

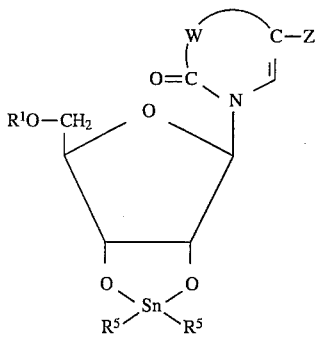

wherein $R^1$ is as defined above, W is —NH—C(NH$_2$), Z is hydrogen and $R^5$ is a $C_1$–$C_6$ alkyl group, with (ii) an amine selected from pyridine and amines having the general formula $$Q^2Q^3Q^4N$$

wherein $Q^2$, $Q^3$ and $Q^4$ can be the same or different and are is selected from the group comprising a $C_1$–$C_6$ alkyl group and a $C_6$–$C_9$ aryl group, in the presence of (iii) a sulfonyl compound having the general formula $$R^6SO_2X$$

wherein $R^6$ is selected from the group comprising —CF$_3$, a $C_1$–$C_6$ alkyl group and $C_6$–$C_9$ aryl group, and X is selected from a halogen and SO$_3$CF$_3$, to produce a compound of Formula II.

In yet another aspect of the present invention, a process is provided for preparing a compound of Formula I, or a pharmaceutically acceptable salt thereof:

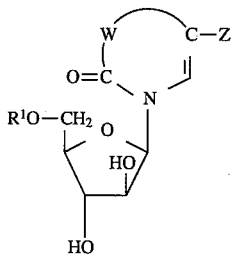

which comprises the step of reacting (i) a compound of Formula III:

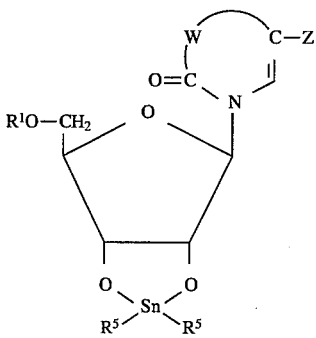

with (ii) an amine selected from pyridine and amines having the general formula $$Q^2Q^3Q^4N$$

wherein $Q^2$, $Q^3$ and $Q^4$ can be the same or different and are selected from the group comprising a $C_1$–$C_6$ alkyl group and a $C_6$–$C_9$ aryl group, in the presence of (iii) a sulfonyl compound having the general formula $$R^6SO_2X$$

wherein $R^6$ is selected from the group comprising —CF$_3$, a $C_1$–$C_6$ alkyl group and $C_6$–$C_9$ aryl group, and X is selected from a halogen and —SO$_3$CF$_3$, to produce a compound of Formula II, and reacting a compound of Formula II or a pharmaceutically acceptable salt thereof with (iv) an amine selected from the group comprising $C_5$–$C_{12}$ heterocyclic amines and amines having the general formula $$R^2R^3R^4N$$

wherein $R^2$, $R^3$ and $R^4$ are as defined above.

DESCRIPTION OF THE PREFERRED EMBODIMENTS

The compound of Formula II:

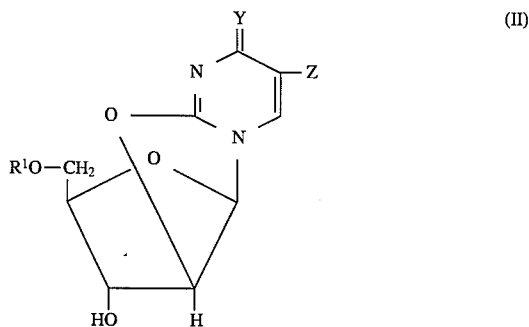

is known. Compounds of Formula II may be prepared in a number of manners; however, preferably, this compound is prepared by reacting a tin oxide conjugate of Formula III. It will of course be understood that the manner in which starting compound of Formula III is made is not particularly restricted as regards the process for making compounds of Formula II.

Preferably, the process for producing a compound of Formula II can be used to produce 2,2'-O-cycloribonucleosides such as 2,2'-O-cyclocytidine, 2,2'-O-cyclouridine, 2,2'-O-cyclothymidine, or pharmaceutically acceptable salts thereof. Generally, 2,2'-O-cycloribonucleosides may be prepared by reacting the appropriate nucleoside with the appropriate dialkyl tin oxide. More preferably, this process is used to produce 2,2'-O-cyclocytidine by reacting a cytidine-compound-tin oxide conjugate of Formula III in which W is —N=C(NH$_2$)— and Z is hydrogen.

In one preferred embodiment of the invention, in which the compound of Formula III is a cytidine conjugate, $R^5$ is butyl and $R^1$ is hydrogen. With these definitions for $R^5$ and $R^1$, the compound of Formula III is 2',3'-O-dibutylstannylene cytidine.

An example of a suitable "$C_2$–$C_6$ allcylacyl group" for use as $R^1$ is acetyl. Further, an example of a suitable "$C_6$–$C_9$ arylacyl group" for use as $R^1$ is benzoyl.

Provided that it does not contain a hydrogen bonded to nitrogen, the amine suitable for use in the process for producing a compound of Formula II is not particularly restricted and may be selected from the group comprising trimethylamine, triethylamine, pyridine, tripropylamine and tributylamine. The most preferred amine is triethylamine.

The reaction of a compound of Formula III with the amine is conducted in the presence of a sulfonyl compound, preferably a sulfonyl chloride compound. More preferably the sulfonyl chloride compound is one of p-toluenesulfonyl chloride and methanesulfonyl chloride.

Typically, the above-noted reaction can be conducted at room temperature, preferably with agitation of the reaction mixture (such as stirring). The reaction may be conducted in any suitable organic solvent system. Examples of suitable organic solvents include: alcohols, toluene, benzene, chloroform, dichloromethane and the like. The preferred organic solvents are alcohols, more preferably methanol.

The most preferred starting material of Formula II for the process of producing a compound of Formula I is 2,2'-O-cyclocytidine in which $R^1$ of Formula II is hydrogen. In this embodiment, the product of Formula I is cytarabine. It will of course be understood that the manner in which starting compound of Formula II is made is not particularly restricted as regards the process of making Formula I.

The amine suitable for use in the process of producing a compound of Formula I is selected from the group comprising $C_5$–$C_{12}$ heterocyclic amines and amines having the general formula $$R^2R^3R^4N$$

wherein $R^2$, $R^3$ and $R^4$ can be the same or different and are selected from the group comprising hydrogen, a $C_1$–$C_6$ alkyl groups and a $C_6$–$C_9$ aryl group, with the proviso that each of $R^2$, $R^3$ and $R^4$ is not hydrogen. Thus, it will be appreciated that the use of ammonia (i.e. $R^2=R^3=R^4=H$) is outside the scope of the present invention. Non-limiting examples of suitable heterocyclic amines include pyridine and piperidine. Non-limiting examples of other amines suitable for use include t-butylamine, trimethylamine, triethylamine, tripropylamine, tributylamine, methylamine, ethylamine, diethylamine and aniline. The most preferred amine suitable for use in the present process is t-butylamine.

Preferably, the process of producing a compound of Formula I is conducted in the presence of an aqueous solvent. Examples of suitable aqueous solvents include water and a mixture of water and at least one other solvent miscible therewith. The most preferred aqueous solvent for use in this process comprises solely water.

Typically, the reaction used to produce a compound of Formula I can be conducted at room temperature, preferably with agitation (such as stirring) of the reaction mixture. The reaction may be conducted in any polar solvent for the starting compound of Formula I. Preferably, the solvent is water.

The crude 2,2'-O-cyclonucleoside precursor product, preferably, 2,2'-O-cyclocytidine, as well as the crude final products, preferably, cytarabine, cytarabine analogues or pharmaceutically acceptable salts thereof, may be separated from the reaction mixture and purified using conventional techniques within the purview of a person skilled in the art. For example, after the reaction is complete, the solvents may be evaporated under vacuum. Crude 2,2'-O-cyclonueleoside may be suspended and refluxed in a suitable medium (e.g. chloroform). Thereafter, the crude 2,2'-O-cyclonucleoside may be purified from water (in which the product is soluble) and alcohol (in which the product is relatively insoluble). The resulting final cytaxabine solid may be suspended and agitated in a suitable medium to produce a purified product. Examples of such media include alcohol and mixtures containing alcohol and water. The preferred alcohol for use is ethanol.

Aspects of the present invention will be described with reference to the following Examples which should not be considered to limit the scope of the invention.

EXAMPLE 1

A 500 mL flask was charged with 50 mL methanol, 1.95 g cytidine and 2 g dibutyl tin oxide. The resulting suspension was refluxed for five hours and then stirred at room temperature for twelve hours. To the mixture was then added triethylamine (7.8 mL) followed by slow addition of p-toluenesulfonyl chloride (10.68 g). The resulting mixture was stirred for twelve hours at room temperature. Thereafter, the solvents were evaporated under vacuum and chloroform (100 mL) was added to the resulting white gum. The chloroform/white gum suspension was refluxed for fifteen minutes and then cooled to room temperature. The resulting white precipitate was filtered and washed with chloroform, and dried to yield 1 g of crude 2,2'-O-cyclocytidine hydrochloride. The crude cyclocytidine hydrochloride was suspended in 5 mL water and the mixture was heated to 60° C. This solution was filtered and the solvent reduced under vacuum to obtain a turbid oil. Ethanol (18 mL) was added and the mixture was stirred at 5° C. for twelve hours. The resulting precipitate was filtered and dried to provide 0.6 g of pure 2,2'-O-cyclocytidine hydrochloride (29% yield). The product was characterized by comparison of its melting point, and NMR and IR spectra with those previously reported for 2,2'-O-cyclocytidine.

EXAMPLE 2

2,2'-O-cyclocytidine hydrochloride (6.5 g) was dissolved in 35 mL water at 80° C. The solution was cooled to room temperature and t-butylamine (2.8 g) was added and the mixture stirred for 2 hours. Thereafter, the solvent was evaporated under vacuum and ethanol (16 g) was added. The mixture was stirred at room temperature for 12 hours. Filtration of the resulting precipitation yielded 5 g of pure cytarabine after drying, which corresponds to a yield of 83%. The product was characterized by comparison of its melting point, and NMR and IR spectra with those previously reported for cytarabine.

What is claimed is:

1. A process for producing a compound of formula II, or a pharmaceutically acceptable salt thereof

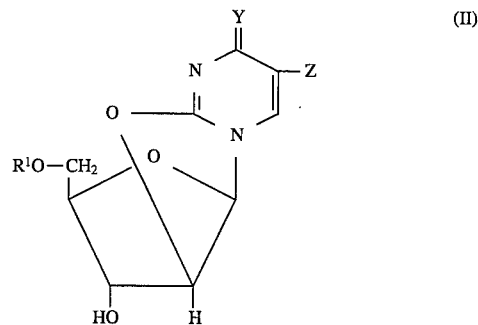

wherein $R^1$ is selected from the group consisting of hydrogen, trityl, methoxytrityl, dimethoxytrityl, acetyl, $C_2$–$C_6$ alkylacyl, allyl, 2,2-trichloroethyl, phosphates and salts thereof, tosyl and mesyl, Z is selected from the group consisting of hydrogen and methyl, and Y is selected from the group consisting of —NH— or O; which process comprises the step of reacting (i) compound of formula III:

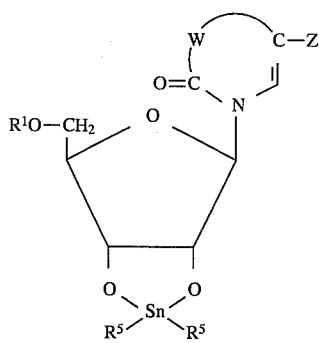

(III)

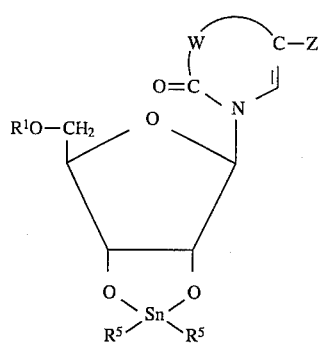

(III)

wherein $R^5$ is a $C_1$–$C_6$ alkyl, $R^1$ and Z have the same meanings as above, and W is selected from the group consisting of —NH—C(O)— and —NH—C(NH$_2$)—, with (ii) an amine selected from the group consisting of pyridine and amines having the formula $Q^2Q^3Q^4N$ whereto $Q^2$, $Q^3$ and $Q^4$ can be the same or different and are selected from the group consisting of a $C_1$–$C_6$ alkyl and a $C_6$–$C_9$ aryl, in the presence of (iii) a sulphonyl compound having the formula $R^6SO_2X$ wherein $R^6$ is selected from the group consisting of —CF$_3$, a $C_1$–$C_6$ alkyl and $C_6$–$C_9$ aryl, and X is selected from the group consisting of —SO$_3$CF$_3$ and a halogen, to produce a compound of formula II.

2. The process defined in claim 1, wherein $R^1$ is hydrogen.

3. The process defined in claim 2, wherein said sulfonyl compound is selected from p-toluenesulfonyl chloride and methanesulfonyl chloride.

4. The process defined in claim 2, wherein said sulfonyl compound is p-toluenesulfonyl chloride.

5. The process defined in claim 4, wherein said amine is triethylamine.

6. The process defined in claim 5, wherein said step is conducted in the presence of methanol.

7. The process defined in claim 1, wherein X is chloride.

8. The process defined in claim 1, wherein said amine is selected from the group consisting of trimethylamine, triethylamine, pyridine, tripropylamine and tributylamine.

9. The process defined in claim 1, wherein said step is conducted in the presence of an organic solvent.

10. The process defined in claim 1, wherein said step is conducted in the presence of an organic solvent selected from the group consisting of alcohols, toluene, benzene, chloroform and dichloromethane.

11. A process for preparing a compound of formula I, or a pharmaceutically acceptable salt thereof

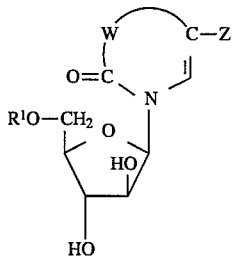

(I)

which comprises the step of reacting (i) a compound of formula III:

wherein $R^1$ is selected from the group consisting of hydrogen, trityl, methoxytrityl, dimethoxytrityl, acetyl, $C_2$–$C_6$ alkylacyl, allyl, 2,2,2-trichloroethyl, phosphates and salts thereof, tosyl and mesyl, $R^5$ is a $C_1$–$C_6$ alkyl group, W is —NH═C(NH$_2$)—; and Z is selected from the group consisting of hydrogen and methyl, with (ii) an amine selected from pyridine and amines having the formula $Q^2Q^3Q^4N$ wherein $Q^2$, $Q^3$ and $Q^4$ can be the same or different and are selected from the group consisting of a $C_1$–$C_6$ alkyl and a $C_6$–$C_9$ aryl, in the presence of (iii) a sulfonyl compound having the formula $R^6SO_2X$ wherein $R^6$ is selected from the group consisting of —CF$_3$, a $C_1$–$C_6$ alkyl and $C_6$–$C_9$ aryl, and X is selected from a halogen or —SO$_3$CF$_3$, to produce a compound of formula II:

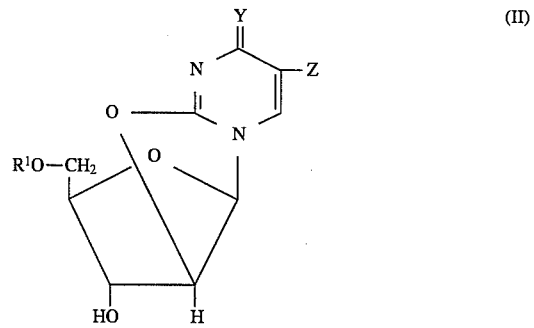

(II)

wherein Y is —NH—, and reacting a compound of formula II or a pharmaceutically acceptable salt thereof with (iv) an amine selected from the group consisting of $C_5$–$C_{12}$ heterocyclic amines and amines having the formula $R^2R^3R^4N$ wherein $R^2$, $R^3$ and $R^4$ can be the same or different and are selected from the group consisting of hydrogen, a $C_1$–$C_6$ alky group and a $C_6$–$C_9$ aryl group, with the proviso that each of $R^2$, $R^3$ and $R^4$ are not hydrogen.

12. The process defined in claim 11, wherein $R^1$ is hydrogen.

13. The process defined in claim 11, wherein the reaction to produce a compound of Formula II is conducted in the presence of an organic solvent, and the subsequent reaction to form a compound of Formula I is conducted in the presence of an aqueous solvent.

14. The process defined in claim 11, wherein the amine used in step (ii) is selected from the group consisting of trimethylamine, triethylamine, pyridine, tripropylamine and tributylamine and the amine used in step (iv) is selected from the group consisting of t-butylamine, tzimethylamine, triethylamine, pyridine, tripropylamine, tributylamine, methylamine, ethylamine, diethylamine, aniline and piperidine.

15. The process defined in claim 14, wherein the amine used in step (ii) is triethylamine and the amine used in step (iv) is t-butylamine.

16. The process defined in claim 11, wherein X is chloride.

17. The process defined in claim 11, wherein said sulfonyl compound is selected from p-toluenesulfonyl chloride or methanesulfonyl chloride.

18. A process for producing a compound of Formula II

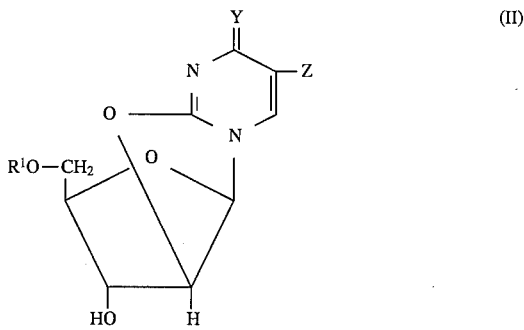

(II)

wherein Y is —N(H)— and Z is hydrogen, or a pharmaceutically acceptable salt thereof, which comprises the step of reacting (i) a compound of Formula III:

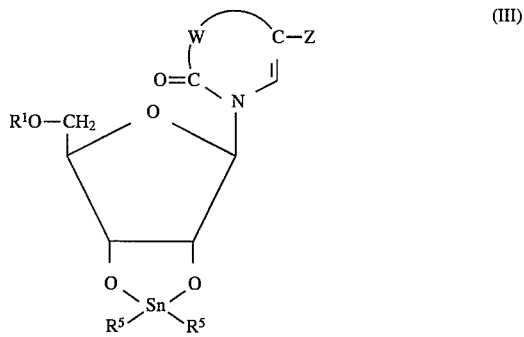

(III)

wherein $R^1$ is selected from the group consisting of hydrogen, trityl, methoxytrityl, dimethoxytrityl, acetyl, a $C_2$–$C_6$ alkylacyl, allyl, 2,2,2-trichloroethyl, phosphates and salts thereof, tosyl and mesyl, W is —NH—C(NH$_2$)—, Z is hydrogen and $R^5$ is a $C_1$–$C_6$ alkyl, with (ii) an amine selected from pyridine and amines of the formula $$Q^2Q^3Q^4N$$

wherein $Q^2$, $Q^3$ and $Q^4$ can be the same or different and are selected from the group consisting of a $C_1$–$C_6$ alkyl and $C_6$–$C_9$ aryl, in the presence of (iii) a sulfonyl compound of the formula $$R^6SO_2X$$

wherein $R^6$ is selected from the group consisting of —$CF_3$, a $C_1$–$C_6$ alkyl and a $C_6$–$C_9$ aryl, and X is selected from a halogen or —$SO_3CF_3$.

19. The process defined in claim 18, wherein $R^1$ is hydrogen.

20. The process defined in claim 18, wherein X is chloride.

21. The process defined in claim 19, wherein said sulfonyl compound is selected from p-toluenesulfonyl chloride or methanesulfonyl chloride.

22. The process defined in claim 19, wherein said sulfonyl compound is p-toluenesulfonyl chloride.

23. The process defined in claim 18, wherein said amine is selected from the group consisting of trimethylamine, triethylamine, pyridine, tripropylamine and tributylamine.

24. The process defined in claim 22, wherein said amine is triethylamine.

25. The process defined in claim 18, wherein said step is conducted in the presence of an organic solvent.

26. The process defined in claim 18, wherein said step is conducted in the presence of an organic solvent selected from the group consisting of alcohols, toluene, benzene, chloroform and dichloromethane.

27. The process defined in claim 24, wherein said step is conducted in the presence of methanol.

28. The process defined in claim 1, wherein Z is hydrogen.

29. The process defined in claim 11, wherein Z is hydrogen.

* * * * *